US007612237B2

(12) United States Patent
Knaup

(10) Patent No.: US 7,612,237 B2
(45) Date of Patent: Nov. 3, 2009

(54) PROCESS FOR PREPARING
β-AMINO-α-HYDROXYCARBOXAMIDES

(75) Inventor: Günter Knaup, Bruchköbel (DE)

(73) Assignee: Degussa GmbH, Dusseldorf (DE)

( * ) Notice: Subject to any disclaimer, the term of this patent is extended or adjusted under 35 U.S.C. 154(b) by 0 days.

(21) Appl. No.: 11/819,964

(22) Filed: Jun. 29, 2007

(65) Prior Publication Data
US 2008/0015368 A1 Jan. 17, 2008

(30) Foreign Application Priority Data
Jul. 4, 2006 (DE) .................. 10 2006 031 202

(51) Int. Cl.
C70C 231/12 (2006.01)
(52) U.S. Cl. .................. 564/197; 564/190; 564/192; 564/193; 564/198; 549/553
(58) Field of Classification Search .................. 549/553; 564/123, 190, 197, 192, 198, 193
See application file for complete search history.

(56) References Cited

U.S. PATENT DOCUMENTS

| 3,538,158 | A * | 11/1970 | Becke et al. .................. 564/153 |
| 6,025,516 | A | 2/2000 | Ramaswamy |
| 6,057,473 | A | 5/2000 | Sharpless |
| 7,034,178 | B2 | 4/2006 | Faber |
| 2003/0153788 | A1 | 8/2003 | Kobayashi |
| 2005/0153900 | A1 | 7/2005 | Velazquez |
| 2005/0197301 | A1 | 9/2005 | Njoroge |

FOREIGN PATENT DOCUMENTS

| DE | 583 243 C | 8/1933 |
| WO | WO-95/00535 | 1/1995 |
| WO | WO 98/42657 | 10/1998 |
| WO | WO-98/42657 | 10/1998 |
| WO | WO-01/74768 | 10/2001 |
| WO | WO-02/18369 | 3/2002 |
| WO | WO 03/087075 A1 | 10/2003 |
| WO | WO 2005/058821 A1 | 6/2005 |
| WO | WO-2005/082892 | 9/2005 |
| WO | WO-2005/087731 | 9/2005 |
| WO | WO-2006/008170 | 1/2006 |
| WO | WO 2007/105729 | 9/2007 |
| WO | WO 2007/109023 A | 9/2007 |
| WO | WO 2007/138928 A1 | 12/2007 |

OTHER PUBLICATIONS

Bols et al., Acta Chemica Scandinavica, 45, 1991, 280-284.*
Fourneau et al., Mémoires présentés à la société chimique, 1940, 7(54), 593-603.*
English language translation for Fourneau et al., Mémoires présentés à la société chimique, 1940, 7(54), 593-603.*
European Search Report for EP 07 11 0343 filed Sep. 20, 2007.
Avakyan, et al., "Oxygen-Containing Heterocycles. Part XVIII. Synthesis and Antiarrhythmic Activity of N-[1-(1,4-Benzodioxan-2-YL)Ethyl]Amides of N-Substituted α-Hydroxy-β-Aminopropionic Acids," Pharmaceutical Chemistry Journal 31(4):178-181 (1997).
Banfi, et al., "Passerini Reaction-Amine Deprotection-Acyl Migration (PADAM): A Convenient Strategy for the Solid-Phase Preparation of Peptidomimetic Compounds," Molecular Diversity 6:227-235 (2003).
Behrens, et al., "Selective Transformations of 2,3-Epoxy Alcohols and Related Derivatives. Strategies for Nucleophilic Attack at Carbon-3 or Carbon-2," J. Org. Chem. 50:5696-5704 (1985).
Cacciola, et al., "The Synthesis of Lysine α-Ketomide Thrombin Inhibitors via an Epoxy Amide Ring Opening," Tetrahedron Letters 38:5741-5744 (1977).
Catalano, et al. "Design of Small Molecular Ketoamide-Based Inhibitors of Cathepsin K," Bioorg. Med. Chem. Lett. 14:719-722 (2004).
Chen, et al., "Potent 7-Hydroxy-1,2,3,4-Tetrahydroisoquinoline-3-Carboxylic Acid-Based Macrocyclic Inhibitors of Hepatitis C Virus NS3 Protease," J. Med. Chem. 49:567-574 (2006).
Chen, et al., "Novel Potent Hepatitis C Virus NS3 Protease Inhibitors Derived from Proline-Based Macrocycles," J. Med. Chem. 49:995-1005 (2006).
Chen, et al., "P1 and P1' Optimization of [3,4]-Bicycloproline P2 Incorporated Tetrapeptidyl α-Ketoamide Based HCV Protease Inhibitors," Lett. Drug Design & Discovery 2:118-123 (2005).
Chong, et al., "Nucleophilic Openings of 2,3-Epoxy Acids and Amides Mediated by Ti(O-i-Pr)$_4$. Reliable C-3 Selectivity," J. Org. Chem. 50:1560-1563 (1985).
Kamandi, et al.,"Die Synthese von β-Phenyl-isoserinen durch Ammonolyse von β-Phenylglycidestern, II," Arch. Pharm. 308:135-147 (1975).
Liwschitz, et al., "Syntheses of α-Amino-βhydroxy-acids," J. Chem. Soc. 1116-1119(1961).
Ohshima, et al., "Catalytic Asymmetric Epoxidation of α,β-Unsaturated Carboxylic Acid Imidazolides and Amides by Lanthanide-Binol Complexes," Tetrahedron 59:10485-10497(2003).
Punniyamurthy, et al., "Polyaniline Supported Cobalt(II) Salen Catalysed Synthesis of Pyrrolidine Containing α-Hydroxyamide Core Structures as Inhibitors for HIV Proteases," Tetrahedron Lett. 38(25): 4463-4466 (1997).
Rubin, et al., "A Highly Efficient Aminohydroxylation Process," Angew Chem. Intl. Ed. Engl. 36(23): 2637-2640 (1997).

(Continued)

Primary Examiner—Bernard Dentz
Assistant Examiner—David E Gallis
(74) Attorney, Agent, or Firm—Law Office of Michael A. Sanzo, LLC

(57) ABSTRACT

The present invention is directed to a process for preparing β-amino-α-hydroxycarboxamides. The process works with epoxycarboxamides of the formula 2

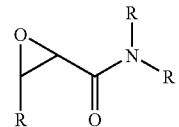

formula 2 which are reacted with ammonia or other amines.

21 Claims, No Drawings

OTHER PUBLICATIONS

Tack, et al., "Unterscheidung N-substituierter 3-Phenylserin-und 3-Phenylisoserin-Derivate," *Arch. Pharm.* 312: 138-147 (1979).

English language translation for reference B8 (DE 583 243) cited above.

English abstract and machine translation of WO 2007/105729, listed as reference B4 above.

English language translation of claims for WO 2007/105729, listed as reference B4 above.

English language abstract for WO 2007/138928, listed as reference B6 above.

English translation of patent claims for WO 2007/138928, listed as reference B6 above.

Hoskins, et al., "A Hexaimidazole Ligand Binding Six Octahedral Metal Ions to Give an Infinite 3D α-Po-Like Network Through Which Two Independent 2D Hydrogen-Bonded Networks Interweave," *Angew. Chem. Int. Ed. Engl.* 36(24):2752-2755 (1997).

Kato, et al., "Regio- and Stereo-specific Synthesis of threo-3-Amino-2-hydroxy-Acids, Novel Amino-acids contained in Aminopeptidase Inhibitors of Microbial Origin," *J.C.S. Perkin I*: 1618-1621 (1980).

English language translation for reference B8 (DE 583 243) cited above, (1933).

* cited by examiner

PROCESS FOR PREPARING β-AMINO-α-HYDROXYCARBOXAMIDES

CROSS REFERENCE TO RELATED APPLICATIONS

The present application claims priority to German application 10 2006 031 202.3, filed on Jul. 4, 2006, which is incorporated in its entirety herein by reference.

FIELD OF THE INVENTION

The present invention is directed to a process for preparing β-amino-α-hydroxycarboxamides. The process works with epoxycarboxamides of the formula 2 formula 2

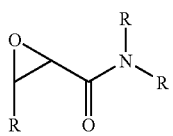

which are reacted with ammonia or other amines.

BACKGROUND OF THE INVENTION

β-amino-α-hydroxycarboxamides are important intermediates for chemical synthesis. They may, for example, be reacted further to 3-amino-2-ketamides. A multitude of recent protease inhibitors contain, as C-terminal units, 3-amino-2-ketoamides. Examples thereof are calpin inhibitors (WO 95/00535), thrombin inhibitors (J. Cacciola et al., Tetrahedron Lett. 38, 5741 (1997)) and, very particularly, a multitude of hepatitis C virus (HCV) protease inhibitors, as detailed, for example, in WO 05/087731, WO 05/058821. Among the latter, VX-950 is mentioned by way of example (WO 01/74768, WO 02/18369), which is already in advanced stages of clinical development.

VX-950

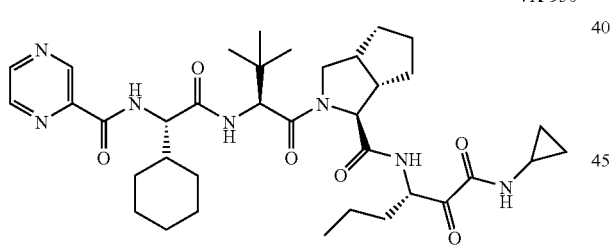

The most commonly used process for preparing 3-amino-2-ketamides consists of the oxidation of the corresponding β-amino-α-hydroxycarboxamides:

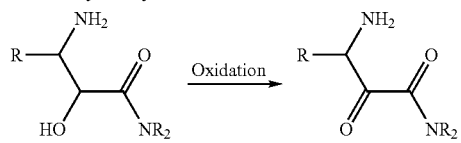

For the preparation of these β-amino-α-hydroxycarboxamides, various processes are employed, which are listed hereinafter by way of example for 3-amino-2-hydroxyhexanoic acid:

1. Condensation of nitroalkanes with glyoxalic acid, reduction of the nitro group and subsequent conversion of the acid to the amide (K. X. Chen, J. Med. Chem. 49, 567, (2006); ibid. 995):

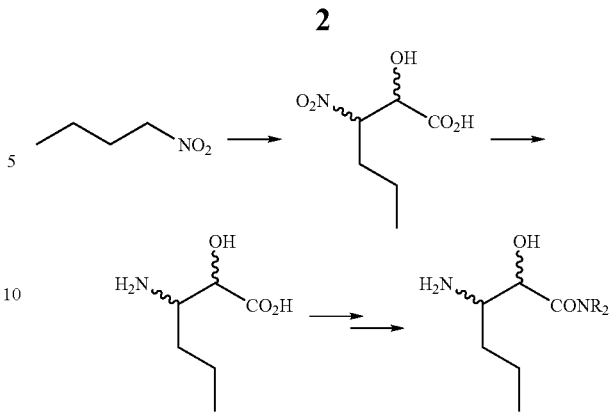

A disadvantage of this process is that the complete range of possible stereoisomeric compounds are obtained, which, after oxidation of the hydroxyl group, lead to mixtures of diastereomeric compounds, which cannot be separated in most cases. If they can, this is possible only with chromatographic methods (K. X. Chen, J. Med. Chem, 49, 995 (2006)).

2. Conversion of protected amino acids to the aldehydes, conversion to the cyanohydrins, hydrolysis thereof to the acid and subsequent conversion to the amides (e.g.: WO 01/74768, WO 02/18369, WO 05/087731, S.-H. Chen, Lett. Drug Design & Discovery, 2005, 118).

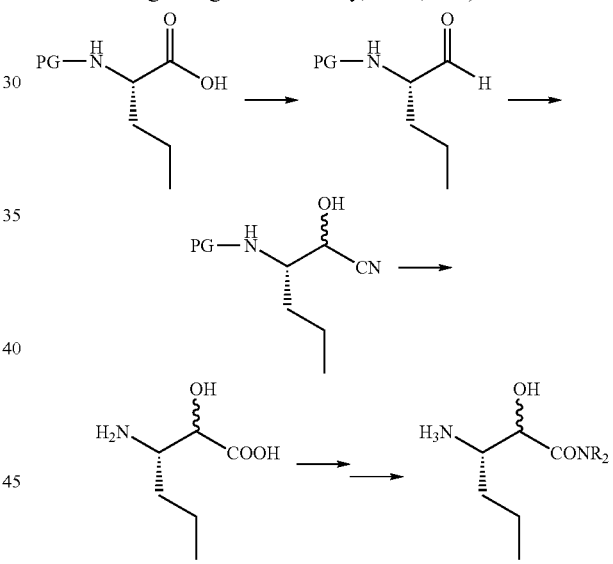

Disadvantages of this process are that the starting materials are expensive and mixtures of the diastereomeric amino alcohols are obtained, which can complicate isolation of intermediates in the synthesis steps which follow. Another disadvantage is that the free aminohydroxy acids are inevitably obtained, for whose conversion to the amides another introduction of an N-protecting group and generally an activation of the acid function are required.

3. By enantioselective aminohydroxylation (Sharpless, Angew, Chem. 109, 2752 (1997); WO 97/46516, WO 98/42657) of acrylic esters (WO 05/087731, US 2005/0197301):

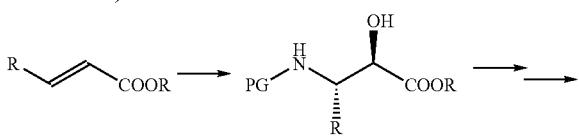

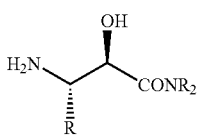

A disadvantage of this process is that large amounts of chiral catalysts and toxic osmium oxide are required as oxidizing agents.

4. Primary amides can, by analogy to point 2, be prepared by reacting the aldehydes with isonitriles and acetic acid (J. G. Catalano, Biorg. Med. Chem. Lett., 14, 719 (2004); D. G. Barrett, ibid. 2543; L. Banfi, Molecular Diversity, 6, 227 (2003), WO 05/087731, US 2005/0197 301):

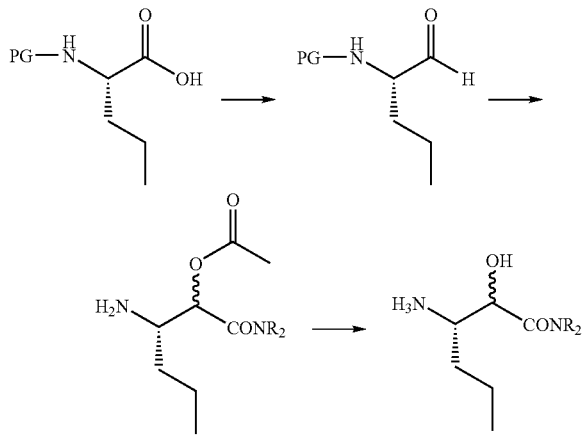

In addition to the disadvantages mentioned under 2., an additional factor in this variant is that the isonitriles required are often not commercially available but rather have to be prepared in a complicated manner.

5. A further possibility consists in the regioselective ring opening of epoxyamides by means of azide and subsequent reduction to amino compounds (J. Cacciola, Tetrahedron Lett. 38, 5741 (1997); US 2003/0153788, K. B. Sharpless, J. Org. Chem. 50, 5696 (1985)).

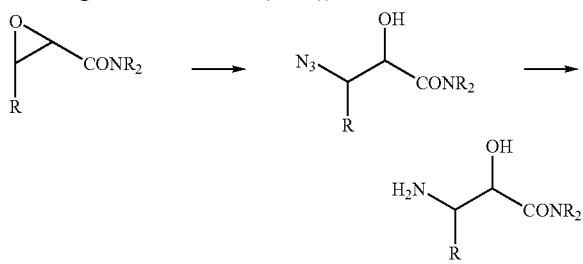

A disadvantage of this variant is that azides have to be used for ring opening, which is problematic from a safety point of view, and an additional reduction step is required for conversion to the amines. For this process, it is also possible to use enantiomerically pure epoxides, which then directly afford a diastereomerically pure amino alcohol. For the preparation of enantiomerically pure epoxides, though, either the corresponding allyl alcohol has to be epoxidized according to Sharpless (J. Cacciola, Tetrahedron Lett. 38, 5741 (1997), US 2003/0153788) or, for the epoxidation of the corresponding acrylic acids, lanthanide complexes (T. Ohshima, Tetrahedron 59, 10485 (2003) have to be used. A direct asymmetric synthesis of epoxide amides is possible by reacting chiral S-alkylthioglycolamides with aldehydes (WO 03/08707).

It is also known that epoxycarboxylic acids and esters can be opened directly with ammonia or amines, preferably benzylamine. In this case, the free acids are opened exclusively by attack at the C-2 atom (e.g.: Y. Liwschitz, J. Chem. Soc., 1961, 1116). An exception is formed by 3-phenylglycidic acid, which reacts with ammonia predominantly to give phenylisoserine (WO 03/003804). Addition of at least stoichiometric amounts of Ti(O-iPr)$_4$ in the reaction of aliphatic acids likewise allows a reversal of selectivity (K. B. Sharpless, J. Org. Chem. 50, 1560 (1985)). Esters, in contrast, are opened preferentially by attack on the C-3 atom (J. Chem. Soc. Perkin I, 1980, 1618). In this case, the esters are converted at least partly to the corresponding amides. A direct reaction of N-substituted epoxyamides with ammonia has to date not found any use, apparently because the amides range between the esters and the acids in the reactivity scale, and it would be expected that mixtures of 2- and 3-substituted aminohydroxamides would be obtained. In the case of reactions with ammonia, transamidations are additionally to be expected under the required reaction conditions. Therefore, the reaction with azides already described above has preferentially been employed.

While the reactions of beta-arylglycidic esters with ammonia and amines have been intensively examined (W. Tack, Arch. Pharm. 312, 138 (1979) and cit. lit; E. Kamandi, Arch. Pharm. 308, 135 (1975) and cit. lit., U.S. Pat. No. 6,025,516, WO 06/008170), little is known about the reaction of aliphatic glycidic esters.

DESCRIPTION OF THE INVENTION

It was an object of the present invention to find a simple route to enantiomerically pure 3-amino-2-hydroxyamides of the formula (I), which proceeds from readily available starting materials, can be performed in a simple manner on the industrial scale and does not require specialized technical apparatus. In particular, the envisaged process should be superior to the prior art processes from an economic and ecological standpoint.

Thus, the invention is directed to a process for preparing compounds of the general formula (I)

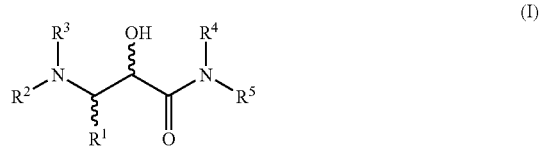

in which $R^1$, $R^2$, $R^3$, $R^4$, $R^5$ are each independently $(C_1-C_8)$-alkyl, HO—$(C_1-C_8)$-alkyl, $(C_2-C_8)$-alkoxyalkyl, $(C_6-C_{18})$-aryl, $(C_{7-19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, or $R^4$ and $R^5$ and/or $R^2$ and $R^3$ together form a $(C_2-C_8)$-alkylene bridge, where $R^1$, $R^2$, $R^3$, $R^4$ may additionally be H and $R^1$ is not phenyl when $R^4$ and/or $R^5$=H, The process involves reacting epoxycarboxamides of the general formula (II):

in which

R¹, R⁴, R⁵ are each as defined above with ammonia or amines of the general formula (III)

(III)

in which

R², R³ are each as defined above. Production of the desired product is achieved in a completely surprising and advantageous manner. Compounds of general formula (I) are obtained in high yields, unexpectedly high regioisomeric purity and, in the case where R¹≠H, with virtually complete retention of the diastereomeric purities.

Preference is given to synthesizing compounds of formula (I) in which:

R¹=(C₁-C₈)-alkyl,
R², R³=H,
R⁴=H, and
R⁵=(C₁-C₈)-alkyl-(C₃₋C₈)-cycloalkyl, especially cyclopropyl.

Particular preference is given to the use of aliphatic epoxycarboxamides of formula (II), especially compounds in which R¹ is a linear alkyl chain having 2-8 carbon atoms, especially a linear C₃-alkyl radical.

Preference is likewise given to using epoxycarboxamides (II) in which at least one of the R⁴, R⁵ radicals is not H. Here, the use of N-alkylepoxycarboxamides is most particularly preferred. The process is most preferably applicable to the N-cyclopropyl-3-propyloxiranecarboxamide of formula 3.

Formula 3

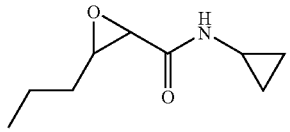

In a particular embodiment, the present invention relates to a process for preparing enantiomerically enriched compounds of general formula (I) in which enantiomerically enriched compounds of formula (II) are used or the racemic diastereomerically enriched compounds of formula (I) which otherwise form are crystallized enantioselectively as the salt with chiral organic acids.

The inventive reaction can be performed in a solvent considered useful for this purpose by a person skilled in the art. Preferred solvents include: water, aqueous and nonaqueous organic solvents. Preference is given to performing the reaction in protic solvents, for example alcohols or water, and very particularly in mixtures thereof (for example ethanol and concentrated aqueous ammonia).

The reaction is preferably performed at a temperature of 0-200° C., more preferably at 20-150° C. and very particularly at 50-100° C., in a pressure vessel at the autogenous pressure which is established.

The invention likewise provides enantiomerically enriched N-cyclopropyl-3-alkyloxiranecarboxamides of the formula (IV)

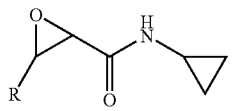

(IV)

in which

R is a linear (C₁-C₈)-alkyl radical.

Preference is given to obtaining and using compounds of formula (IV) in which R is a linear C₃-alkyl radical. Preference is additionally given to compounds of the formula (IV) in which the substituents are in trans positions (2S,3R or 2R, 3S). Compounds of the formula (IV) are novel and can be used effectively for the preparation of compounds of the formula V.

A further aspect of the present invention is that of salts of the compounds of the formula (V)

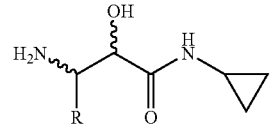

(V)

in which

R is a linear (C₁-C₈)-alkyl radical with chiral acids, for example hydroxyl acids (e.g. mandelic acid, tartaric acid, dibenzoyltartaric acid, ditolyltartaric acid, lactic acid), N-acylamino acids (e.g. benzyloxycarbonyl-L-phenylalanine, acetyl-L-phenylalanine) or sulphonic acids (e.g. camphorsulphonic acid) or aminodicarboxylic acids. Preference is given to forming salts of the compounds of the formula (V) with mandelic acid and benzyloxycarbonylphenylalanine. Very particular preference is given to salts with benzyloxycarbonyl-L-phenylalanine.

Particular preference is given to salts of the compounds of the formula (V) with acids in which the 2S, 3S isomer is enantiomerically enriched by more than 90%, preferably 92%, more preferably 95% and most preferably more than 97%. Exceptionally preferred are salts of 2S,3S compounds of the formula (V) with optically active acids. In principle, all salts considered useful by the person skilled in the art may be used for salt formation. Preference is given to the organic acids mentioned below for the classical optical resolution. Particularly useful salts include (2S,3S)—N-cyclopropyl-3-amino-2-hydroxy-hexanamide (S)-mandelic acid salt or the corresponding (2R,3R)—(R)-mandelic acid salt, and the (2S, 3S—N-cyclopropyl-3-amino-2-hydroxyhexanamide N-benzyloxycarbonyl-L-phenylalanine salt and the corresponding (2R,3R)-phenylalanine salt.

The epoxycarboxamides of the formula (II) may be prepared by processes known to those skilled in the art, for example in a simple manner from the corresponding acids and the amines of the formula HNR⁴R⁵. The epoxycarboxylic acids may be activated, using methods well known in peptide chemistry (see for example, Houben-Weyl Vol. 15, Synthesis of Peptides, Thieme Verlag Stuttgart 1974). Preference is given, however, to preparing these compounds as described in US 2003/0153788 by means of mixed anhydrides and very particularly by means of pivaloyl chloride. Particular preference is given to using alkali metal salts of the epoxycarboxylic acids, very particularly potassium salts, for the reaction with the acid chlorides.

The epoxycarboxylic acids may occur as 4 different stereoisomers. The process according to the invention preferably proceeds such that the erythro-aminohydroxy compounds of the formula (I) form stereoselectively from the trans-epoxide amides of the formula (II), while the cis compounds result selectively in the corresponding threo compounds. Use of the enantiomerically pure epoxycarboxamides of the formula (II) where R¹≠H results in the corresponding aminohydroxy compounds of the formula (I) in which the configuration at C atom 3 is exchanged compared to the epoxy compound.

Highly enantiomerically enriched, virtually pure trans- and cis-epoxycarboxamides (II) can be prepared with retention of stereochemistry from the corresponding epoxycarboxylic acids by the methods discussed above. The starting materials in turn are obtainable stereoselectively by achiral epoxidation (EP 618202, K. B. Sharpless, J. Org. Chem. 50, 1979 (1985)) of the corresponding E- or Z-acrylic acids or esters thereof. In addition, as described, for example, in US 2003/0153788, an enantioselective epoxidation to the enantiomerically enriched epoxy alcohols and subsequent oxidation to the epoxycarboxylic acids can be performed.

A further commonly used method for preparing epoxycarboxylic acid derivatives is Darzen glycidic ester synthesis. Starting from aldehydes and haloacetic esters, predominantly the trans compounds are formed. Similar results are obtained in the reaction of carbonyl compounds with sulphur ylides (WO 03/087075). In many cases, the pure trans compounds can then be obtained by crystallizing the corresponding epoxycarboxylic acid salts. This has the further advantage that these salts can be reacted directly with acid chlorides to give the mixed anhydrides and these in turn, if appropriate in one pot, to the amides.

As already indicated, enantiomerically pure and diastereomerically pure derivatives of the compounds of the general formula (I), more preferably the erythro compounds thereof, are prepared by salt pair formation with chiral acids, for example hydroxyl acids (e.g. mandelic acid, tartaric acid, dibenzoyltartaric acid, ditolyltartaric acid, lactic acid), N-acylamino acids (e.g. benzyloxycarbonyl-L-phenylalanine, acetyl-L-phenylalanine) or sulphonic acids (e.g. camphorsulphonic acid). Preference is given to forming salts of the compounds of the formula (I) with mandelic acid and benzyloxycarbonylphenylalanine. Preference is accordingly likewise given to a process according to the invention in which the racemic diastereomerically enriched compounds of the formula (I) formed are crystallized enantioselectively as the salt with chiral organic acids.

Salt formation is performed preferably with 0.2-2.0 equivalents, better 0.3-1.0 equivalent, very preferably 0.5-0.6 equivalent, of the chiral acid. The solvents used are, depending on the solubility of the salts, organic solvents such as alcohols, esters, ethers, hydrocarbons. Particular preference is given to using alcohols such as ethanol and isopropanol, and acetic esters such as ethyl acetate, n-butyl acetate and isopropyl acetate. To increase the solubility, a little water can also be added to the solvents. Preference is given to dissolving the compounds of the formula (I) and the chiral acid under hot conditions and to crystallizing the salts by cooling.

The free bases of the compounds of formula (I) can be obtained from the salts by known processes, for example acid-base extraction. Salt exchange with stronger acids, for example hydrochloric acid, is also possible.

The invention likewise provides for the preparation of pharmacologically active compounds using salts of compounds of formula V

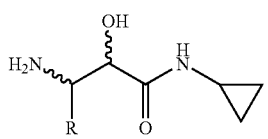

(V)

in which
R is a linear $(C_1-C_8)$-alkyl radical with chiral acids.

"$(C_1-C_8)$-Alkyl" radicals are considered to be methyl, ethyl, n-propyl, isopropyl, n-butyl, isobutyl, sec-butyl, tert-butyl, pentyl, hexyl, heptyl or octyl including all of their bonding isomers.

"$(C_1-C_8)$-alkoxy" radical corresponds to the $(C_1-C_8)$-alkyl radical with the proviso that it is bonded to the molecule via an oxygen atom.

"$(C_2-C_8)$-Alkoxyalkyl" means radicals in which the alkyl chain is interrupted by at least one oxygen function, where two oxygen atoms may not be joined to one another. The number of carbon atoms specifies the total number of carbon atoms present in the radical.

A "$(C_2-C_8)$-alkylene bridge" is a carbon chain having two to eight carbon atoms, this chain being bonded to the molecule in question via two different carbon atoms. It can be a saturated or unsaturated carbocyclic or heterocyclic ring having 1-4 nitrogen, silicon, sulphur, phosphorus or oxygen atoms in the ring system.

The radicals described in the preceding paragraphs may be mono- or polysubstituted by halogens and/or nitrogen-, oxygen-, phosphorus-, sulphur-, silicon-containing radicals. These are in particular alkyl radicals of the type mentioned above which have one or more of these heteroatoms in their chain or which are bonded to the radical via one of these heteroatoms.

"$(C_3-C_8)$-Cycloalkyl" is understood to mean cyclopropyl, cyclobutyl, cyclopentyl, cyclohexyl or cycloheptyl radicals, etc. which may be substituted by one or more halogens and/or nitrogen-, oxygen-, phosphorus-, sulphur-, silicon-containing radicals and/or have nitrogen, oxygen, phosphorus, sulphur atoms in the ring, for example 1-, 2-, 3-, 4-piperidyl, 1-, 2-, 3-pyrrolidinyl, 2-, 3-tetrahydrofuryl, 2-, 3-, 4-morpholinyl.

A "$(C_3-C_8)$-cycloalkyl-$(C_1-C_8)$-alkyl radical" denotes a cycloalkyl radical as detailed above, which is bonded to the molecule via an alkyl radical as specified above.

In the context of the invention, $(C_1-C_8)$-acyloxy means an alkyl radical as defined above which has a maximum of 8 carbon atoms and is bonded to the molecule via a COO function.

In the context of the invention, $(C_1-C_8)$-acyl means an alkyl radical as defined above which has max. 8 carbon atoms and is bonded to the molecule via a CO function.

A "$(C_6-C_{18})$-aryl radical" is understood to mean an aromatic radical having 6 to 18 carbon atoms. In particular, this includes compounds such as phenyl, naphthyl, anthryl, phenanthryl, biphenyl radicals, or systems of the above-described type fused to the molecule in question, for example indenyl systems which may optionally be substituted by halogen, $(C_1-C_8)$-alkyl, $(C_1-C_8)$-alkoxy, $NH_2$, $NH(C_1-C_8)$-alkyl, $N((C_1-C_8)$-alkyl$)_2$, OH, $CF_3$, $NH(C_1-C_8)$-acyl, $N((C_1-C_8)$-acyl$)_2$, $(C_1-C_8)$-acyl, $(C_1-C_8)$-acyloxy.

A "$(C_7-C_{19})$-aralkyl radical" is a $(C_6-C_{18})$-aryl radical bonded to the molecule via a $(C_1-C_8)$-alkyl radical.

In the context of the invention, a "$(C_3-C_{18})$-heteroaryl radical" denotes a five-, six- or seven-membered aromatic ring system composed of 3 to 18 carbon atoms and having heteroatoms, for example nitrogen, oxygen or sulphur, in the ring. Such heteroaromatics are considered in particular to be radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. This radical may be substituted with the same radicals as the above mentioned aryl radical.

A "$(C_4\text{-}C_{19})$-heteroaralkyl" is understood to mean a heteroaromatic system corresponding to the $(C_7\text{-}C_{19})$-aralkyl radical.

Useful halogens (Hal) include fluorine, chlorine, bromine and iodine.

The term "enantiomerically enriched" or "enantiomeric excess" is understood, in the context of the invention, to mean the proportion of one enantiomer in a mixture with its optical antipode in a range of >50% and <100%. The ee is calculated as follows:

([enantiomer1]−[enantiomer2])/([enantiomer1]+ [enantiomer2])=ee.

The term "diastereomerically enriched" refers to the proportion of one diastereomer in a mixture with the other possible diastereomers of the compound in question.

Unless otherwise indicated, the structures of compounds disclosed herein includes all theoretically possible diastereomers and enantiomers which can occur as a result of varying the configuration at the corresponding carbon atoms.

EXAMPLES

Example 1

N-Cyclopropyl-trans-3-n-propyloxirane carboxamide 200 g of trans-3-n-propyloxiranecarboxylic acid potassium salt are suspended in 2 l of acetone, admixed with 120 g of triethylamine and cooled to 3° C. 146 g of pivaloyl chloride are then added, and the mixture is stirred at 20° C. for 20 minutes and then cooled to 3° C. To this are added 82 g of cyclopropylamine in 175 ml of acetone. After stirring for 20 min, the solution is drawn off in vacuo, and the residue is dissolved in 2 l of toluene and 400 ml of water, and the pH is adjusted to 10. The aqueous phase is removed and the organic phase is admixed with 300 ml of water and the pH is adjusted to 2 with hydrochloric acid. The organic phase is removed and concentrated in vacuo. 175 g of N-cyclopropyl-trans-3-n-propyloxiranecarboxamide are obtained as a light brown oil.

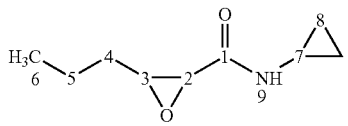

$^1$H NMR of N-cyclopropyl-trans-propyloxiranecarboxamide (500 MHz, DMSO, 303 K):

| δ/ppm | Multiplicity | Intensity | Assignment |
|---|---|---|---|
| 0.40-0.65 | m | 4 | 8 |
| 0.91 | t | 3 | 6 |
| 1.42/1.54 | m/m | 1/1 | 4 |
| 1.24 | m | 2 | 5 |
| 1.60 | s (broad) | 2 | NH$_2$ |
| 2.64 | m | 1 | 7 |
| 2.97 | m | 1 | 3 |
| 3.10 | d | 1 | 2 |
| 7.98 | d | 1 | NH 9 |

Example 2

N-Cyclopropyl-erythro-3-amino-2-hydroxyhexanamide a) with Anhydrous Ammonia 183 g of N-cyclopropyl-trans-3-n-propyloxiranecarboxamide are dissolved in 1683 g of 10.5% by weight ethanolic ammonia and heated to 100° C. in a closed autoclave for 6 h. Thereafter, the mixture is cooled to room temperature; the solvent is removed in vacuo. The residue is suspended in 700 ml of toluene, very substantially concentrated again and diluted with fresh toluene. Heating to reflux dissolves the residue. After cooling to 0° C. and filtering-off, 136 g of N-cyclopropyl-erythro-3-amino-2-hydroxyhexanamide are obtained.

m.p.: 101-104° C.

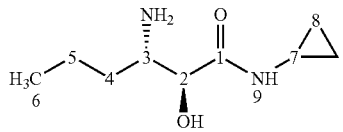

$^1$H NMR of N-cyclopropyl-S,S/R,R-3-amino-2-hydroxyhexanamide (500 MHz, DMSO, 303 K)

| δ/ppm | Multiplicity | Intensity | Assignment |
|---|---|---|---|
| 0.40-0.65 | m | 4 | 8 |
| 0.83 | t | 3 | 6 |
| 1.13/1.43 | m/m | 1/1 | 4 |
| 1.24 | m | 2 | 5 |
| 1.60 | s (broad) | 2 | NH$_2$ |
| 2.65 | m | 1 | 7 |
| 2.79 | m | 1 | 3 |
| 3.69 | d | 1 | 2 |
| 5.31 | s (broad) | 1 | OH |
| 7.68 | d | 1 | NH 9 | b) with Aqueous Ammonia 161 g of N-cyclopropyl-trans-3-n-propyloxiranecarboxamide are dissolved in 405 g of 25% by weight ammonia and heated to 90° C. in a closed autoclave for 3 h. Distilling off the excess ammonia in vacuo affords 576 g of a 44.3% by weight aqueous solution which can be used directly for optical resolution.

Example 3

(2S,3S)—N-cyclopropyl-3-amino-2-hydroxyhexanamide (S)-mandelic acid salt 83.8 g of N-cyclopropyl-erythro-3-amino-2-hydroxyhexanamide and 34.4 g of (S)-mandelic acid are dissolved at 70° C. in 1500 ml of isopropanol. The precipitate which forms after cooling to 2° C. is filtered off and recrystallized twice from isopropanol. 42 g of (2S,3S)—N-cyclopropyl-3-amino-2-hydroxyhexanamide (S)-mandelic acid salt are obtained.

m.p.: 132-134° C.

chiral HPLC: 0.3% (R,R)-isomer.

Example 4

N-Cyclopropyl-(2S,3S)-3-amino-2-hydroxyhexanamide N-benzyloxycarbonyl-L-phenylalanine salt 18.6 g of N-cyclopropyl-erythro-3-amino-2-hydroxyhexanamide and 15.9 g of N-benzyloxycarbonyl-L-phenylalanine are dissolved at reflux temperature in 400 ml of ethyl acetate and 33 ml of water. The precipitate which forms after cooling to 0° C. is filtered off and recrystallized from ethanol. 16.7 g of (2S,3S)—N-cyclopropyl-3-amino-2-hydroxyhexanamide N-benzyloxycarbonyl-L-phenylalanine salt are obtained.

m.p.: 195-197° C.

chiral HPLC: R,R-diastereomer: <0.3%

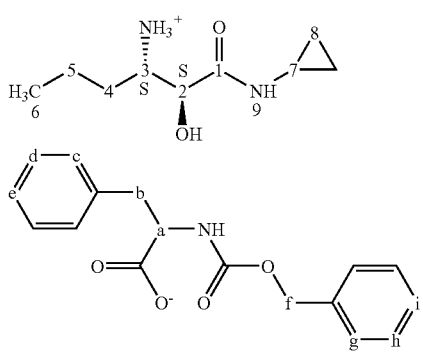

$^1$H NMR of (2S,3S)—N-cyclopropyl-3-amino-2-hydroxy-hexanamide* Z-phenylalanine (500 MHz, DMSO, 303 K)

| δ/ppm | Multiplicity | Intensity | Assignment |
|---|---|---|---|
| 0.45-0.65 | m | 4 | 8 |
| 0.84 | t | 3 | 6 |
| 1.23/1.37 | m/m | 2 | 4 |
| 1.37 | m | 2 | 5 |
| 2.68 | m | 1 | 7 |
| 2.85/3.09 | dd/dd | 2 | b |
| 3.28 | m | 1 | 3 |
| 3.99 | m | 1 | a |
| 4.11 | d | 1 | 2 |
| 4.96 | dd | 2 | f |
| 6.78 | d | 1 | NH Z |
| 7.1-7.4 | m | 10 | 2 * Phe |
| 7.95 | d | 1 | NH 9 |

Example 5

(2S,3S)—N-cyclopropyl-3-amino-2-hydroxy hexanamide hydrochloride 38.7 g of (2S,3S)—N-cyclopropyl-3-amino-2-hydroxyhexanamide (S)-mandelic acid salt are suspended in 500 ml of isopropyl acetate and admixed with 11.8 g of 37% hydrochloric acid. After stirring at room temperature for 1 h, half of the solvent is distilled off in vacuo and replaced by fresh isopropyl acetate. After this has been repeated once more, the mixture is heated to 60° C., and the solid is filtered off and washed with warm isopropyl acetate. 25.0 g of (2S,3S)—N-cyclopropyl-3-amino-2-hydroxyhexanamide hydrochloride are obtained.

m.p.: 212-215° C.

HPLC: R,S/S,R-diastereomers: <0.1% chiral HPLC: R,R-diastereomer: <0.3%

All references cited herein are fully incorporated by reference in their entirety. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for preparing enantiomerically enriched compounds of general formula (I)

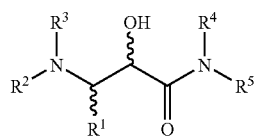 (I)

in which

R$^1$, R$^2$, R$^3$, R$^4$, R$^5$ are each independently (C$_1$-C$_8$)-alkyl, HO—(C$_1$-C$_8$)-alkyl, (C$_2$-C$_8$)-alkoxyalkyl, (C$_6$-C$_{18}$)-aryl, (C$_7$-C$_{19}$)-aralkyl, (C$_3$-C$_{18}$)-heteroaryl, (C$_4$-C$_{19}$)-heteroaralkyl, (C$_1$-C$_8$)-alkyl-(C$_6$-C$_{18}$)-aryl, (C$_1$-C$_8$)-alkyl-(C$_3$-C$_{18}$)-heteroaryl, (C$_3$-C$_8$)-cycloalkyl, (C$_1$-C$_8$)-alkyl-(C$_3$-C$_8$)-cycloalkyl, (C$_3$-C$_8$)-cycloalkyl-(C$_1$-C$_8$)-alkyl, or R$^4$ and R$^5$ and/or R$^2$ and R$^3$ together form a (C$_2$-C$_8$)-alkylene bridge, where R$^1$, R$^2$, R$^3$, R$^4$ may additionally be H and with the proviso that R$^1$ is not phenyl when R$^4$ and/or R$^5$=H, said process comprising:

a) reacting epoxycarboxamides of general formula (II)

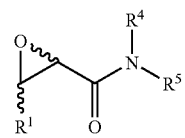 (II)

in which R$^1$, R$^4$, R$^5$ are each as defined above, with ammonia or amines of the general formula (III)

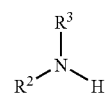 (III)

in which R$^2$, R$^3$ are each as defined above; wherein enantiomerically enriched compounds of general formula (I) are prepared using enantiomerically enriched compounds of formula (II); or as a second step b) enantioselectively crystallizing the salts of racemic diastereomerically enriched compounds of formula (I) using a chiral organic acid;

and wherein one or more of the following conditions apply:

i) R$^1$ is a (C$_1$-C$_8$)-alkyl;

ii) R$^4$ is H;

iii) R$^5$ is a (C$_1$-C$_8$)-alkyl-(C$_3$-C$_8$)-cycloalkyl;

iv) R$^5$ is cyclopropyl.

2. The process of claim 1, wherein the reaction between said epoxycarboxamides and said ammonia or amines is performed at a temperature of 0-200° C. at the autogenous pressure.

3. The process of claim 2, wherein the reaction between said epoxycarboxamides and said ammonia or amines is performed at a temperature of 20-150° C. at the autogenous pressure.

4. The process of claim 2, wherein the reaction between said epoxycarboxamides and said ammonia or amines is performed at a temperature of 50-100° C. at the autogenous pressure.

5. The process of claim 2, wherein the reaction between said epoxycarboxamides and said ammonia or amines is performed in a solvent selected from the group consisting of: water, and aqueous or nonaqueous organic solvents.

6. The process of claim 1, wherein the reaction between said epoxycarboxamides and said ammonia or amines is performed at a temperature of 0-200° C. at the autogenous pressure.

7. The process of claim 6, wherein the reaction between said epoxycarboxamides and said ammonia or amines is performed at a temperature of 20-150° C. at the autogenous pressure.

8. The process of claim 6, wherein the reaction between said epoxycarboxamides and said ammonia or amines is performed at a temperature of 50-100° C. at the autogenous pressure.

9. The process of claim 6, wherein the reaction between said epoxycarboxamides and said ammonia or amines is performed in a solvent selected from the group consisting of: water, and aqueous or nonaqueous organic solvents.

10. The process of claim 1, wherein $R^1$ is a ($C_1$-$C_8$)-alkyl.

11. The process of claim 1, wherein $R^4$ is H.

12. The process of claim 1, wherein $R^5$ is ($C_1$-$C_8$)-alkyl-($C_3$-$C_8$) cycloalkyl.

13. The process of claim 12, wherein $R^1$ is a ($C_1$-$C_8$)-alkyl.

14. The process of claim 13, wherein $R^2$ and $R^3$ are H.

15. The process of claim 14, wherein $R^4$ is H.

16. The process of claim 1, wherein $R^5$ is cyclopropyl.

17. The process of claim 16, wherein $R^1$ is a ($C_1$-$C_8$)-alkyl.

18. The process of claim 17, wherein $R^2$, $R^3$ and $R^4$ are H.

19. The process of claim 1, wherein said chiral organic acid is an N-acylamino acid, a sulphonic acid or an aminodicarboxylic acid.

20. The process of claim 1, wherein said chiral organic acid is selected from the group consisting of: mandelic acid, dibenzoyltartaric acid, ditolyltartaric acid, lactic acid, acetyl-L-phenylalanine and camphorsulphonic acid.

21. The process of claim 1, wherein said chiral organic acid is benzyloxycarbonyl-L-phenylalanine.

* * * * *